US012754611B2

(12) United States Patent
Xu et al.

(10) Patent No.: US 12,754,611 B2
(45) Date of Patent: Oct. 6, 2026

(54) AFFECTIVE HAPTIC REGULATION METHOD BASED ON MULTIMODAL FUSION

(71) Applicant: SOUTHEAST UNIVERSITY, Jiangsu (CN)

(72) Inventors: Baoguo Xu, Jiangsu (CN); Xin Wang, Jiangsu (CN); Jiajin Wang, Jiangsu (CN); Aiguo Song, Jiangsu (CN)

(73) Assignee: SOUTHEAST UNIVERSITY, Jiangsu (CN)

( * ) Notice: Subject to any disclaimer, the term of this patent is extended or adjusted under 35 U.S.C. 154(b) by 247 days.

(21) Appl. No.: 18/817,208

(22) Filed: Aug. 27, 2024

(65) Prior Publication Data

US 2025/0076986 A1 Mar. 6, 2025

Related U.S. Application Data

(63) Continuation of application No. PCT/CN2023/127190, filed on Oct. 27, 2023.

(30) Foreign Application Priority Data

Sep. 1, 2023 (CN) ......................... 202311121644.1

(51) Int. Cl.

*G06F 3/01* (2006.01)
*G06V 10/80* (2022.01)
*A61B 5/16* (2006.01)

(52) U.S. Cl.

CPC ............ *G06F 3/016* (2013.01); *G06V 10/806* (2022.01); *A61B 5/165* (2013.01); *G06F 2203/011* (2013.01)

(58) Field of Classification Search

CPC . G06F 3/016; G06F 2203/011; G06V 10/806; A61B 5/165

(Continued)

(56) References Cited

U.S. PATENT DOCUMENTS

2011/0207100 A1* 8/2011 Brokken ................. G06F 3/015 434/236
2014/0232534 A1* 8/2014 Birnbaum ................ G08B 6/00 340/407.1
2021/0350917 A1* 11/2021 Curtis .................... A61B 5/165

FOREIGN PATENT DOCUMENTS

CN 114035686 2/2022
CN 114356095 4/2022

(Continued)

OTHER PUBLICATIONS

"International Search Report (Form PCT/ISA/210) of PCT/CN2023/127190", mailed on Apr. 9, 2024, pp. 1-3.

(Continued)

*Primary Examiner* — Nathan P Brittingham
(74) *Attorney, Agent, or Firm* — JCIPRNET

(57) ABSTRACT

Disclosed are an affective haptic regulation system and method based on multimodal fusion, including a haptic optimal parameter adjustment module, a haptic generation module, a visual-auditory generation module, a multi-physiological signal acquisition module, a multi-sensory signal acquisition module, and a multimodal fusion emotion recognition module. The system can fuse multi-physiological signal features with audio and haptic modal features by acquiring a plurality of physiological signals of a user, accurately identify a current affective state of the user in real time through advanced data processing and analysis technology, seek for a haptic parameter with the help of an optimization theory, and achieve proactive regulation of affective state of the user; and the system can overcome the limitations of traditional subjective scale methods, effectively reduce the influence of unstable physiological signals on emotion recognition results, and significantly improve the accuracy of affective detection in the affective haptic regulation system.

9 Claims, 6 Drawing Sheets

(58) Field of Classification Search
USPC .......................................................... 345/173
See application file for complete search history.

(56) References Cited

FOREIGN PATENT DOCUMENTS

| | | |
|---|---|---|
| CN | 114779930 | 7/2022 |
| CN | 115984829 | 4/2023 |

OTHER PUBLICATIONS

"Written Opinion of the International Searching Authority (Form PCT/ISA/237) of PCT/CN2023/127190", mailed on Apr. 9, 2024, pp. 1-3.

* cited by examiner

AFFECTIVE HAPTIC REGULATION METHOD BASED ON MULTIMODAL FUSION

CROSS-REFERENCE TO RELATED APPLICATION

This application is a continuation of PCT application No. PCT/CN2023/127190, filed on Oct. 27, 2023, which claims a priority benefit to China patent application No. CN202311121644.1 filed on Sep. 1, 2023. The entirety of the above-mentioned patent applications are hereby incorporated by reference herein and made a part of this specification.

TECHNICAL FIELD

The present disclosure belongs to the technical field of emotion regulation, and particularly relates to an affective haptic regulation system and method based on multimodal fusion.

BACKGROUND

In recent years, the rapid development of affective computing and haptic technology has given rise to an emerging field: affective haptics. Affective computing aims to reveal a mechanism of emotion generation and expression, while haptic technology focuses on simulating human haptic sensing. Integrating affective information with haptic technology, affective haptics aims to explore the potential of using haptic technology in affective detection, display, and communication, providing new possibilities for human-computer interaction.

As core technology in the field of affective haptics, an affective haptic regulation system aims to perceive an affective state of an individual in real time, and guide it through haptic stimuli, thereby achieving proactive affective regulation during an interaction process. The affective haptic regulation system has promising applications in the fields of human-computer interaction, such as medical rehabilitation and audio-visual entertainment. For example, in the medical field, the affective haptic regulation system provides innovative methods for affective disorders such as depression by assisting in affective regulation through haptic stimuli. In the field of audio-visual entertainment, the affective haptic regulation system enhances affective immersion through haptic stimuli, creating a more immersive experience for a user.

However, despite broad prospects of the affective haptic regulation system, there are still some technical difficulties that are imperative to be solved:

1. Lack of objective and real-time emotion detection means. Existing emotion detection methods for the affective haptic regulation system often rely on subjective evaluation tools such as scales, which are prone to interference from individual subjective awareness and external environments, resulting in limited objectivity and real-time nature of affective states.
2. Unclear mechanisms of how haptic stimuli affect the affective states. Although haptics is closely associated with emotion, there is still a lack of clear guidance on how to adjust specific haptic parameters to achieve expected affective regulation, which making the system difficult to achieve the desired affective regulation effect in practical applications.

The foregoing two technical difficulties restrict further development of the affective haptic regulation system.

SUMMARY

In order to solve the above problems, the present disclosure discloses an affective haptic regulation system and method based on multimodal fusion, the system fuses multi-physiological signal features with audio and haptic modal features by acquiring a plurality of physiological signals of a user, such as EEG and ECG signals, and can accurately identify a current affective state of the user in real time in combination with advanced data processing and analysis technology, seek a haptic parameter with the help of an optimization theory, and achieve proactive regulation of affective state by applying haptic stimuli to the user.

In order to achieve the above objective, the present disclosure adopts a following technical solution:

an affective haptic regulation system based on multimodal fusion, including a haptic optimal parameter adjustment module, a haptic generation module, a visual-auditory generation module, a multi-physiological signal acquisition module, a multi-sensory signal acquisition module, and a multimodal fusion emotion recognition module. The haptic optimal parameter adjustment module automatically solves an optimal haptic parameter according to a difference between current emotion and target emotion of the user, and sends the optimal haptic parameter to the haptic generation module and generates a haptic effect; the haptic generation module and the visual-auditory generation module cooperate to generate visual-auditory-haptic fusion stimuli to act on the user, so as to regulate and control emotions of the user; the multi-physiological signal acquisition module and the multi-sensory signal acquisition module acquire various physiological signals, audio signals and haptic vibration signals of the user in real time, and the signals are inputted to the multimodal fusion emotion recognition module to detect a current affective state of the user, which is then sent back to the haptic optimal parameter adjustment module to form a closed-loop affective haptic regulation system.

As a core of the affective haptic regulation system based on multimodal fusion, the haptic optimal parameter adjustment module automatically seeks for a haptic parameter with the help of an optimization theory according to the difference between the current affective state and the target emotion of the user, and sends the haptic parameter to the haptic generation module to ensure the effectiveness of affective regulation. The haptic optimal parameter adjustment module includes a haptic parameter optimization model and a haptic parameter solving module. The haptic parameter optimization model is expressed as:

$$\min_{f,q,r,c} \gamma\sum_{i=1}^{n}\|M_i(f, q, r, c) - M_{bi}\|_2^2 + \mu\|S(f, q, r, c) - S_b\|_2^2 + \varphi\|P(f, q, r, c)\|_2^2$$

$$\text{s.t. } 0 \le P \le P_m$$

$$0 \le f \le f_m$$

$$0 \le q \le q_m$$

$$0 \le r \le r_m$$

in the formulae, $M_i$ is an actual power value of a certain electrode i on a brain topographic map, $M_{bi}$ is a reference power value of the certain electrode i on the brain topographic map, Sis a calculated affective state value, $S_b$ is a target affective state value, P is an actual power value consumed by the haptic generation module, $P_m$ is a set maximum power value consumed by the haptic generation module, $f_m$ is a set maximum haptic vibration frequency, $q_m$ is a set maximum haptic vibration intensity, $r_m$ is a set maximum haptic vibration rhythm, and γ, μ and φ are weight coefficients of the haptic parameter optimization model.

The haptic parameter solving module adopts a particle swarm optimization algorithm, reinforcement learning, and other machine learning algorithms, to solve four parameters in the haptic parameter optimization model, that is, a haptic vibration frequency f, a haptic vibration intensity q, a haptic vibration rhythm r, and a haptic vibration position c, and to send the solved parameters to the haptic generation module.

The haptic generation module is a wearable device capable of expressing haptic sensation through vibration, including a vibration vest, a vibration bracelet, vibration gloves, and the like, and the haptic generation module is configured to transmit specific haptic experience to the user by setting a vibration frequency, a vibration intensity, a vibration rhythm and a vibration position of a haptic generation device. The haptic generation module exhibits continuous presence of a background haptic vibration that changes adaptively with audio, and at the same time, another haptic expression can be realized based on the four parameters calculated by the haptic parameter optimization model, and the haptic expression corporates with the background haptic vibration to effectively enhance affective experience of the user.

The visual-auditory generation module provides the user with visual and auditory stimuli, including movie clips of different emotion types. The movie clips are conducive to guiding the user to enter a specific affective state, where audio of the movie clips provides a basis for changes in the background haptic vibration.

The multi-physiological signal acquisition module acquires a plurality of physiological signals of the user in real time, including 64-channel electroencephalogram (EEG) signals and electrocardiogram (ECG) signals, where the EEG signals are acquired by an EEG signal acquisition module, and the EEG signal acquisition module is composed of a 64-channel actiCAP electrode cap and an EEG amplifier from Brain Products GmbH. The ECG signals are acquired by an ECG signal acquisition module, which is an ActiveTwo series high-channel ECG acquisition system from Biosemi B. V.

The multi-sensory signal acquisition module includes an auditory signal acquisition module and a haptic signal acquisition module, which are capable of acquiring audio signals generated in the visual-auditory generation module in real time, and acquiring the haptic vibration signals generated in the haptic generation module in real time, respectively.

The multimodal fusion emotion recognition module is capable of analyzing, processing and recognizing the current affective state of the user according to multi-physiological signals of the user and multi-sensory signals of emotion elicitation materials, and then sending a signal of the current affective state to the haptic optimal parameter adjustment module for intelligent regulation of a haptic parameter. The multimodal fusion emotion recognition module includes a signal preprocessing module, a feature extraction module, a feature fusion module, and an emotion decoding module. The signal preprocessing module pre-processes the acquired EEG signals and the ECG signals, including downsampling, filtering, artifact removal, and the like. The feature extraction module extracts features from the audio signals, the haptic vibration signals, the preprocessed EEG signals and ECG signals, respectively. The feature fusion module performs feature fusion on the multi-physiological signal features, audio features extracted from the audio signals and vibration features extracted from the haptic vibration signals by using a feature fusion algorithm. The emotion decoding module classifies the multimodal fusion features by using a classification algorithm to obtain the current affective state of the user. The multimodal fusion emotion recognition module has the advantage of fusing the multi-physiological signal features with audio and haptic modal features, which can effectively reduce the influence of unstable physiological signals on emotion recognition results.

The present disclosure has the beneficial effects:

1. The affective haptic regulation system in the present disclosure adopts an affective detection method based on multimodal fusion, fuses the multi-physiological signal features with the audio and haptic modal features, overcomes the limitations of traditional subjective scale methods, effectively reduces the influence of unstable physiological signals on emotion recognition results, and significantly improves the accuracy of affective detection in the affective haptic regulation system.
2. The haptic optimal parameter adjustment module in the present disclosure can seek a haptic parameter with the help of an optimization theory by analyzing the difference between the current affective state and the target emotion of the user in real time, such that haptic stimuli can more accurately guide and adjust the affective state of the user, and the effect and efficiency of the affective haptic regulation system are effectively improved.
3. The affective haptic regulation system and method based on multimodal fusion in the present disclosure can establish the affective haptic database of the user, and generate personalized haptic patterns using big data and large model learning technology to present customized affective experience.

REFERENCE NUMERALS IN THE ACCOMPANYING DRAWINGS

1. haptic optimal parameter adjustment module; 2. haptic generation module; 3. visual-auditory generation module; 4. multi-physiological signal acquisition module; 5. multi-sensory signal acquisition module; 6. multimodal fusion emotion recognition module; 7. haptic parameter optimization model; 8. haptic parameter solving module; 9. EEG signal acquisition module; 10. ECG signal acquisition module; 11. auditory signal acquisition module; 12. haptic signal acquisition module; 13. signal preprocessing module; 14. feature extraction module; 15. feature fusion module; and 16. emotion decoding module.

DETAILED DESCRIPTIONS OF THE EMBODIMENTS

The present disclosure will be further illustrated below with reference to the accompanying drawings and specific embodiments. It should be understood that the following specific embodiments are only used to illustrate the present disclosure, but are not intended to limit the scope of the present disclosure.

Embodiment 1

Figure 1:
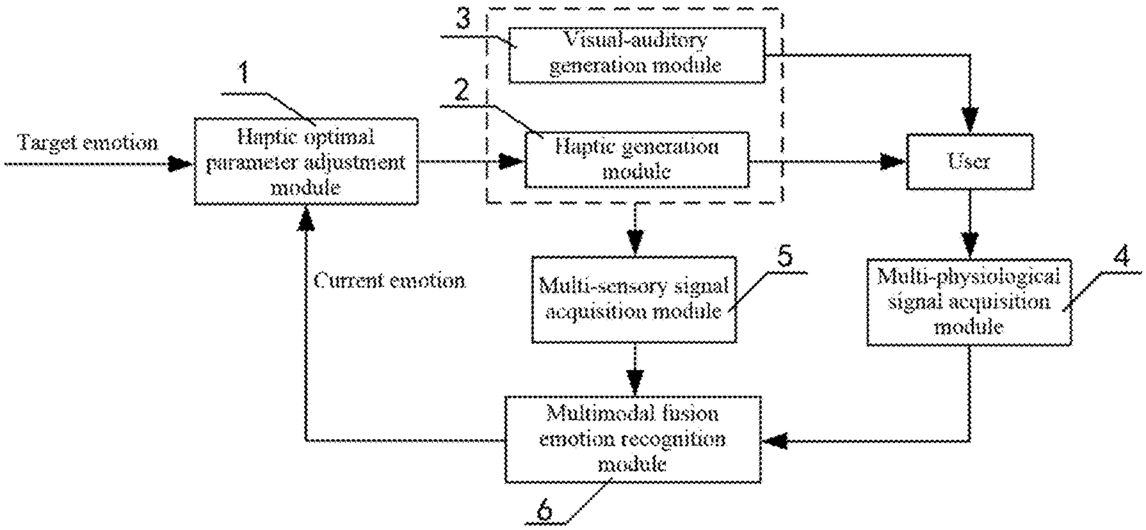
FIG. 1 is a functional block diagram of an affective haptic regulation method based on multimodal fusion according to the present disclosure.

This embodiment describes an affective haptic regulation system based on multimodal fusion, with an overall schematic diagram shown in FIG. 1, and the system includes a haptic optimal parameter adjustment module 1, a haptic generation module 2, a visual-auditory generation module 3, a multi-physiological signal acquisition module 4, a multi-sensory signal acquisition module 5, and a multimodal fusion emotion recognition module 6. The haptic optimal parameter adjustment module 1 automatically solves an optimal haptic parameter according to a difference between current emotion and target emotion of a user, and sends the optimal haptic parameter to the haptic generation module 2 and generates a haptic effect; the haptic generation module 2 and the visual-auditory generation module 3 cooperate to generate visual-auditory-haptic fusion stimuli to act on the user, so as to regulate and control emotions of the user; the multi-physiological signal acquisition module 4 and the multi-sensory signal acquisition module 5 acquire various physiological signals, audio signals and haptic vibration signals of the user in real time, and input the same to the multimodal fusion emotion recognition module 6 to detect a current affective state of the user, and give feedback to the haptic optimal parameter adjustment module 1 to form the closed affective haptic regulation system based on multimodal fusion.

Figure 2:
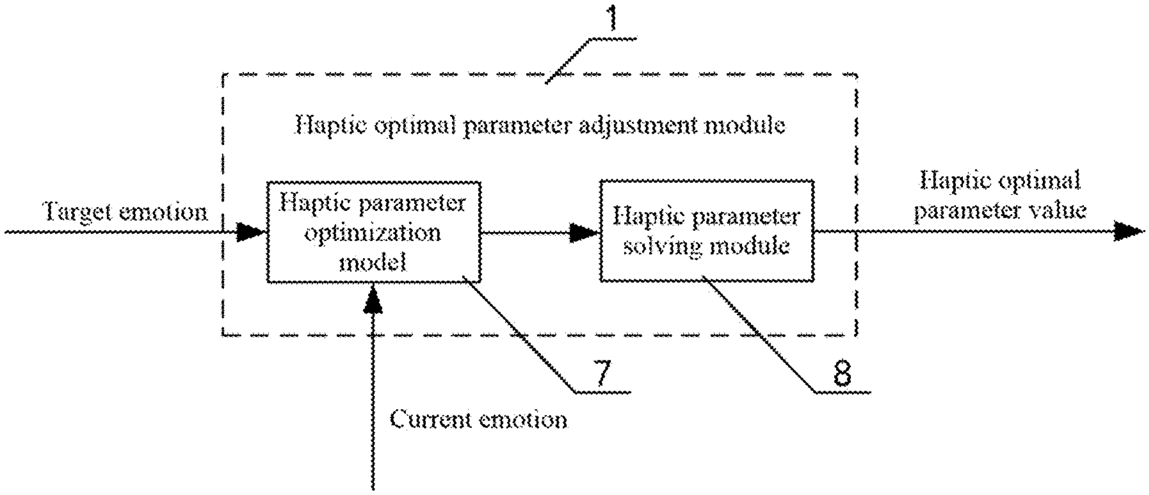
FIG. 2 is a schematic diagram of a haptic optimal parameter adjustment module according to the present disclosure.

Referring to FIG. 2, FIG. 2 is a schematic diagram of the haptic optimal parameter adjustment module 1. As a core of the affective haptic regulation system based on multimodal fusion, the haptic optimal parameter adjustment module 1 automatically seeks for a haptic parameter with the help of an optimization theory according to the difference between the current affective state and the target emotion of the user, and sends the haptic parameter to the haptic generation module 2 to ensure the effectiveness of affective regulation. The haptic optimal parameter adjustment module 1 includes a haptic parameter optimization model 7 and a haptic parameter solving module 8.

The haptic parameter optimization model 7 establishes a reliable mathematical model based on elements such as an electroencephalogram signal, an affective state, and vibration consumption power, and is configured to adaptively adjust four key parameters in the haptic generation module 2, including a haptic vibration frequency f, a haptic vibration intensity q, a haptic vibration rhythm r, and a haptic vibration position c. The haptic parameter optimization model 7 is expressed as:

$$\min_{f,q,r,c} \gamma\sum_{i=1}^{n}\|M_i(f,q,r,c)-M_{bi}\|_2^2+\mu\|S(f,q,r,c)-S_b\|_2^2+\varphi\|P(f,q,r,c)\|_2^2$$

$$\text{s.t. } 0\le P\le P_m$$

$$0\le f\le f_m$$

$$0\le q\le q_m$$

$$0\le r\le r_m$$

in the formulae, $M_i$ is an actual power value of a certain electrode i on a brain topographic map, $M_{bi}$ is a reference power value of the certain electrode i on the brain topographic map, Sis a calculated affective state value, $S_b$ is a target affective state value, P is an actual power value consumed by the haptic generation module, $P_m$ is a set maximum power value consumed by the haptic generation module, $f_m$ is a set maximum haptic vibration frequency, $q_m$ is a set maximum haptic vibration intensity, $r_m$ is a set maximum haptic vibration rhythm, and γ, μ and φ are weight coefficients of the haptic parameter optimization model 7.

The haptic parameter solving module 8 adopts an optimization algorithm, machine learning, reinforcement learning, and the like, and is configured to solve the four parameters in the haptic parameter optimization model 7, that is, the haptic vibration frequency f, the haptic vibration intensity q, the haptic vibration rhythm r, and the haptic vibration position c, and to send the solved parameters to the haptic generation module 2.

Figure 3:
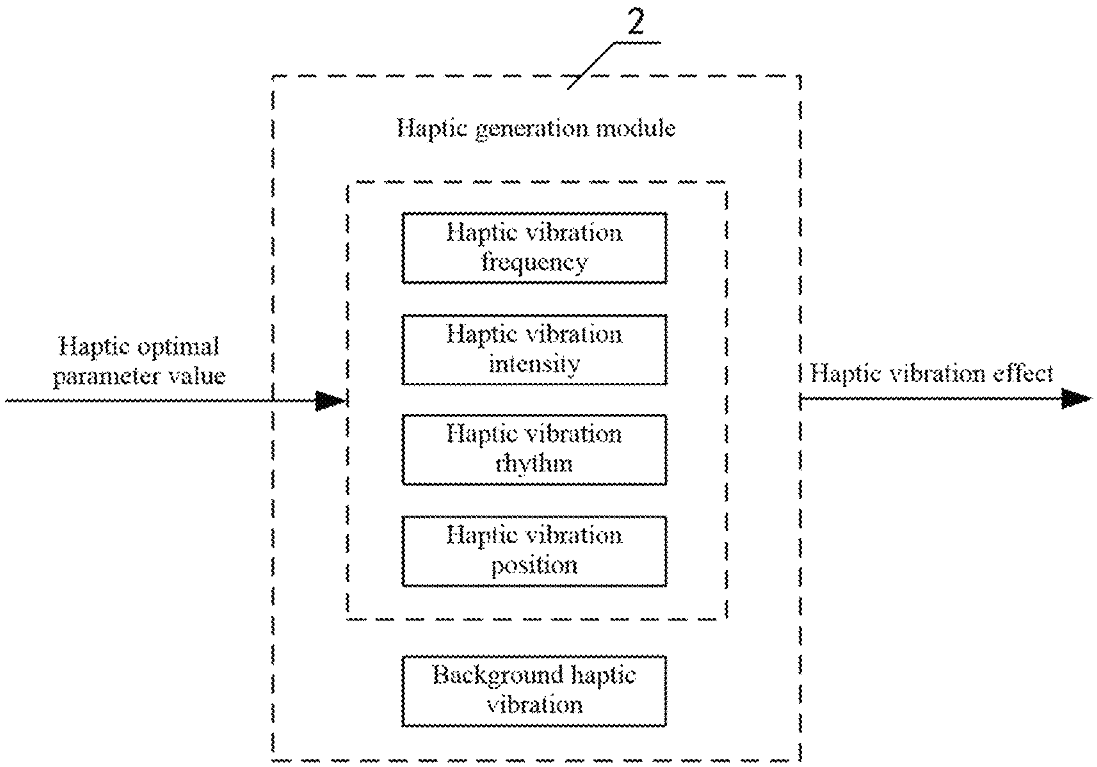
FIG. 3 is a schematic diagram of a haptic generation module according to the present disclosure.

Referring to FIG. 3, FIG. 3 is a schematic diagram of the haptic generation module 2. The haptic generation module 2 is a wearable device capable of expressing haptic sensation through vibration, including a vibration vest, a vibration bracelet, vibration gloves, and the like, and the haptic generation module is configured to transmit haptic experience specific to the user by setting a vibration frequency, a vibration intensity, a vibration rhythm and a vibration position of a haptic generation device. The haptic generation module 2 exhibits continuous presence of a background haptic vibration that changes adaptively with audio, and at the same time, another haptic expression can be realized based on the four parameters calculated by the haptic parameter optimization model 1, and the haptic expression corporates with the background haptic vibration to effectively enhance affective experience of the user. It should be noted that the background haptic vibration persists throughout the entire experiment, and can automatically adjust the vibration intensity and the vibration rhythm according to an audio volume being played. Specifically, the vibration intensity is positively correlated with the audio volume, and the vibration rhythm is adjusted by setting a certain volume threshold, and when the audio volume is lower than the volume threshold, no vibration is generated. An objective of the haptic background design is to make the haptic vibration interacted with audio content in real time, and to bring immersive affective experience to the user by adjusting the vibration intensity and the vibration rhythm. Furthermore, the haptic vibration parameter determined by the haptic optimal parameter adjustment module 1 is not affected by the audio content, but the parameters such as the vibration intensity and the vibration frequency are dynamically optimized according to a real-time affective state of the user, such that a more accurate emotion regulation effect is achieved.

The visual-auditory generation module 3 provides the user with visual and auditory stimuli, including movie clips of different emotion types, and guides the user to enter a specific affective state. Specifically, visual-auditory material includes 16 movie clips of about 4 minutes, covering four types of emotion: happiness, sadness, fear and calmness, that is, each of the types of emotion corresponds to 4 movie clips. Audio of the movie clips provides a basis for changes in the background haptic vibration for the haptic generation module 2, and the visual-auditory stimuli cooperate with the haptic stimuli to further enhance the affective experience of the user.

Figure 4:
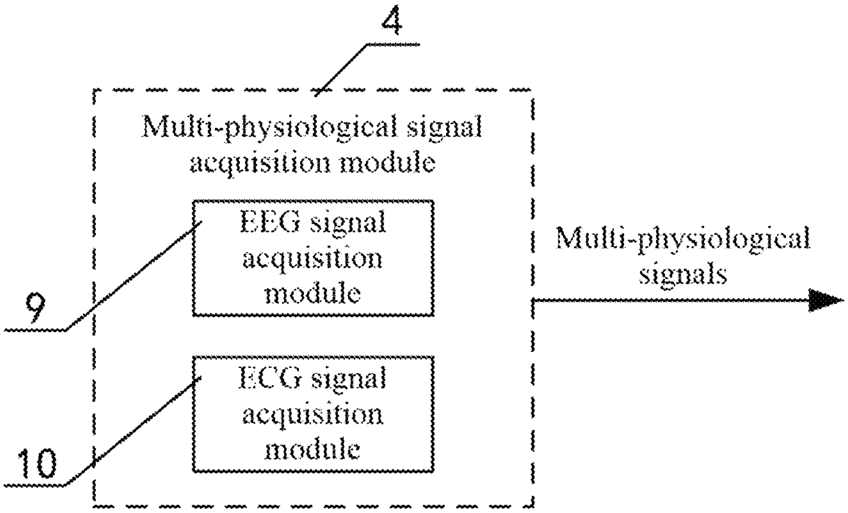
FIG. 4 is a schematic diagram of a multi-physiological signal acquisition module according to the present disclosure.

Referring to FIG. 4, FIG. 4 is a schematic diagram of the multi-physiological signal acquisition module 4. The multi-physiological signal acquisition module 4 acquires a plurality of physiological signals of the user in real time, including 64-channel electroencephalogram (EEG) signals and electrocardiogram (ECG) signals, where the EEG signals are acquired by an EEG signal acquisition module 9, the EEG signal acquisition module 9 is composed of a 64-channel actiCAP electrode cap and an EEG amplifier from Brain Products GmbH. The ECG signals are acquired by an ECG signal acquisition module 10, where the ECG signal acquisition module 10 is an Active Two series high-channel ECG acquisition system from Biosemi B.V.

Figure 5:
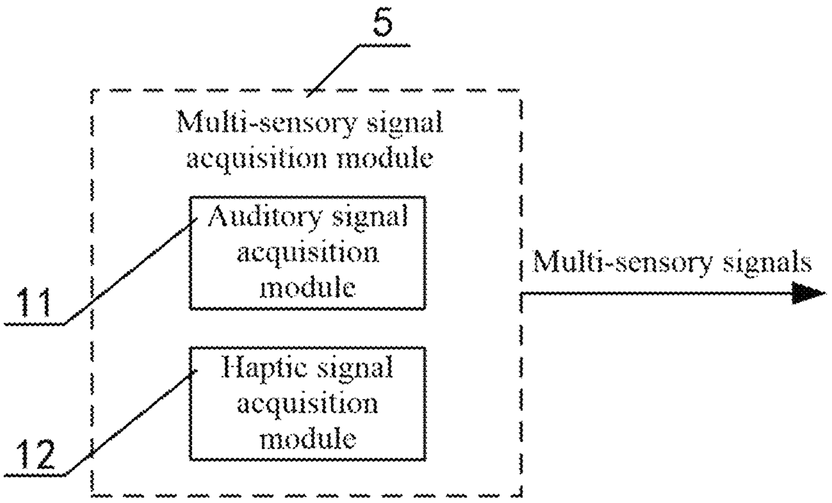
FIG. 5 is a schematic diagram of a multi-sensory signal acquisition module according to the present disclosure.

Referring to FIG. 5, FIG. 5 is a schematic diagram of the multi-sensory signal acquisition module 5. The multi-sensory signal acquisition module 5 includes an auditory signal acquisition module 11 and a haptic signal acquisition module 12, where the auditory signal acquisition module 11 is capable of acquiring audio signals generated in the visual-auditory generation module 3 in real time, and the haptic signal acquisition module 12 is capable of acquiring the haptic vibration signals generated in the haptic generation module 2 in real time.

Figure 6:
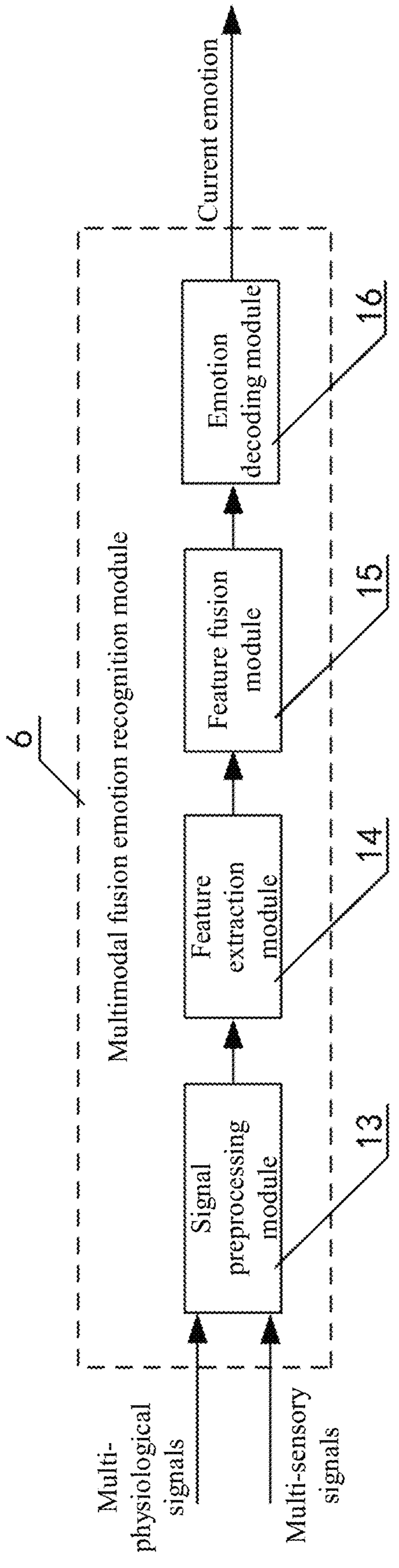
FIG. 6 is a schematic diagram of a multimodal fusion emotion recognition module according to the present disclosure.

Referring to FIG. 6, FIG. 6 is a schematic diagram of the multimodal fusion emotion recognition module 6. The multimodal fusion emotion recognition module 6 is capable of analyzing, processing and recognizing the current affective state of the user according to multi-physiological signals of the user and multi-sensory signals of emotion elicitation materials, and then sending a signal of the current affective state to the haptic optimal parameter adjustment module 1 for intelligent regulation of a haptic parameter. The multimodal fusion emotion recognition module 6 includes a signal preprocessing module 13, a feature extraction module 14, a feature fusion module 15, and an emotion decoding module 16. The signal preprocessing module 13 pre-processes the acquired EEG signals and the ECG signals, including downsampling, filtering, artifact removal, and the like. The feature extraction module 14 extracts features from the multi-sensory signal, the preprocessed EEG signal and ECG signal, respectively. Specifically, feature extraction methods of the EEG signal includes power spectral density, differential entropy, differential asymmetry, rational asymmetry, offline wavelet analysis, statistical features (mean, variance), and the like. A feature extraction manner of the ECG signal includes heart rate and heart rate variability, and the like. The feature fusion module 15 performs feature fusion on the multi-physiological signal feature extracted by the feature extraction module 14, audio features extracted from the audio signals and vibration features extracted from the haptic vibration signals by using a feature fusion algorithm. Specifically, the feature fusion algorithm includes weighted average, principal components analysis, deep belief network, and the like. The emotion decoding module 16 classifies the multimodal fusion features obtained by the feature fusion module 15 by using a classification algorithm to obtain the current affective state of the user. Specifically, the classification algorithm includes support vector machine, logistic regression, Naive Bayes model, deep learning, and the like. The multimodal fusion emotion recognition module 6 has the advantage of considering the instability of physiological signals, especially the EEG signal, and fusing multi-physiological signal features with audio and haptic modal features, which can effectively reduce the influence of unstable physiological signals on emotion recognition results, thereby improving the performance of emotion recognition.

Embodiment 2

Figure 7:
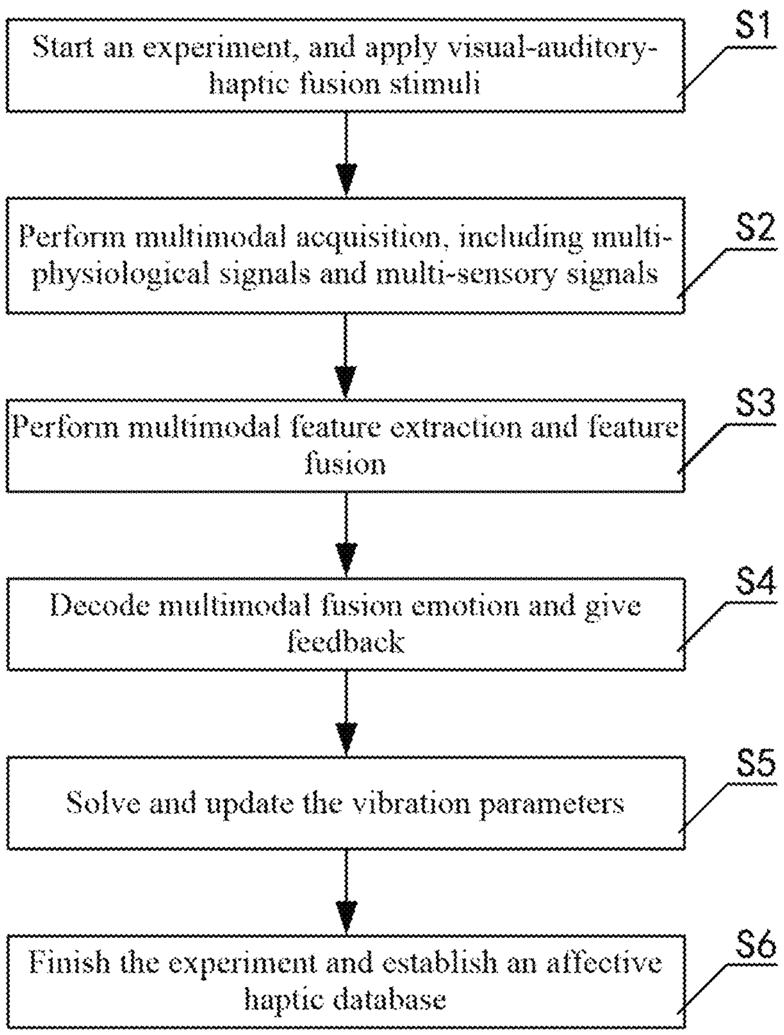
FIG. 7 is a flowchart of an affective haptic regulation method based on multimodal fusion according to the present disclosure.
Figure 8:
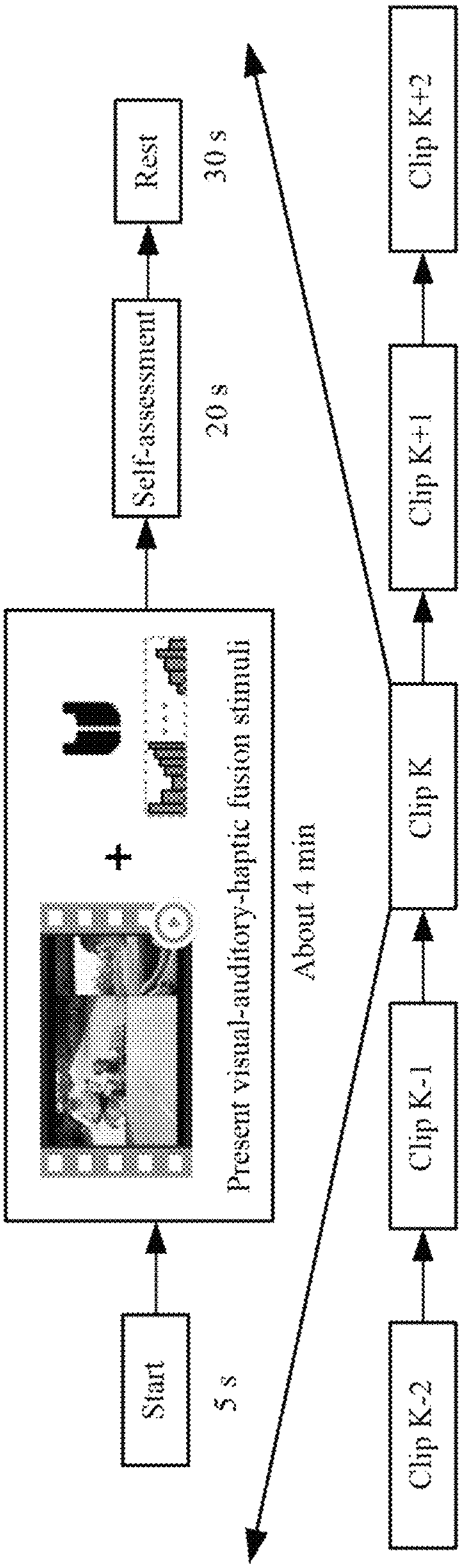
FIG. 8 is an experimental paradigm diagram of an affective haptic regulation method based on multimodal fusion according to the present disclosure.

This embodiment provides a technical solution: an affective haptic regulation method based on multimodal fusion. Referring to FIG. 7, FIG. 7 is a flowchart of the affective haptic regulation method based on multimodal fusion, with specific implementation steps as follows:

Step S1: starting an experiment, and applying visual-auditory-haptic fusion stimuli. The user is guided into different affective states by presenting visual-auditory stimuli and haptic stimuli. Referring to FIG. 8, FIG. 8 is an experimental paradigm diagram of an affective haptic regulation method based on multimodal fusion. Specifically, the visual-auditory stimuli are composed of 16 movie clips of about 4 minutes, covering four types of emotion: happiness, sadness, fear and calmness, that is, each of the types of emotion corresponds to 4 movie clips. The haptic stimuli include continuous presence of the background haptic vibration that changes adaptively with audio, and a haptic effect with vibration parameters determined by the haptic optimal parameter adjustment module. After each of the movie clips ends, the user conducts a self-assessment of 20 s, that is, actual feeling of the movie clips, which is used to verify the effectiveness of the experiment. Afterwards, the user will rest for 30 s to prepare for a next round of playing of the move clips.

Step S2: performing multimodal acquisition, including multi-physiological signals and multi-sensory signals. EEG signals, ECG signals, the audio signals, and haptic vibration signals of the user are acquired in real time. The EEG signals are acquired by the EEG signal acquisition module composed of the 64-channel actiCAP electrode cap and the EEG amplifier from Brain Products GmbH; the ECG signals are acquired by the ECG signal acquisition module composed of the ActiveTwo series high-channel ECG acquisition system from Biosemi B.V.; the audio signals are acquired by the auditory signal acquisition module, and the haptic vibration signals are acquired by the haptic signal acquisition module.

Step S3: performing multimodal feature extraction and feature fusion. The acquired EEG signals and the ECG signals are preprocessed, including downsampling, filtering, artifact removal, and the like, to ensure the quality and stability of the signals. Features are then extracted from the preprocessed EEG and ECG signals to obtain EEG and ECG signal features of the user, and these features can capture variation patterns of different physiological signals in different affective states. Furthermore, the audio features are extracted from the audio signals, and the haptic vibration features are extracted from the haptic vibration signals. The feature fusion algorithm is adopted to fuse the multi-physiological signal features with the audio features and the haptic vibration features to enhance the accuracy and robustness of emotion recognition.

Step S4: decoding multimodal fusion emotion and giving feedback. The multimodal fusion features are classified by using the classification algorithm to obtain the current affective state of the user, and the current affective state is then sent back to the haptic optimal parameter adjustment module.

Step S5: solving and updating the vibration parameters. The haptic optimal parameter adjustment module receives the current affective state of the user, automatically solves the optimal haptic parameter according to the difference between the current emotion and the target emotion, and sends the optimal haptic parameter to the haptic generation module and generates the haptic effect, so as to ensure that the applied haptic stimuli match an actual affective need of the user.

Step S6: finishing the experiment and establishing an affective haptic database. Completion of the playing of the 16 movie clips indicates that the entire experiment is finished, and the haptic the vibration parameters corresponding to different affective states of the user are the analyzed, and the affective haptic database of the user is then established. Different haptic vibration parameters are mapped to different affective states, and a personalized haptic mode is generated to present diverse affective experience for the user.

It should be noted that the above content merely illustrates the technical idea of the present disclosure and cannot limit the protection scope of the present disclosure, those of ordinary skill in the art may also make some modifications and improvements without departing from the principle of the present disclosure, and these modifications and improvements should also fall within the protection scope of the claims of the present disclosure.

What is claimed is:

1. An affective haptic regulation system based on multimodal fusion, comprising a haptic optimal parameter adjustment module, a haptic generation module, a visual-auditory generation module, a multi-physiological signal acquisition module, a multi-sensory signal acquisition module, and a multimodal fusion emotion recognition module, wherein the haptic optimal parameter adjustment module automatically solves an optimal haptic parameter according to a difference between current emotion and target emotion of a user, and sends the optimal haptic parameter to the haptic generation module and generates a haptic effect; wherein the haptic generation module and the visual-auditory generation module cooperate to generate visual-auditory-haptic fusion stimuli to act on the user, so as to regulate and control emotions of the user;

wherein the multi-physiological signal acquisition module and the multi-sensory signal acquisition module acquire various physiological signals, audio signals and haptic vibration signals of the user in real time, and the signals are inputted to the multimodal fusion emotion recognition module to detect a current affective state of the user, which is then sent back to the haptic optimal parameter adjustment module to form a closed-loop affective haptic regulation system wherein one or more processors are configured to execute instructions to perform functions of the haptic optimal parameter adjustment module and the multimodal fusion emotion recognition module, wherein the haptic optimal parameter adjustment module comprises a haptic parameter optimization model and a haptic parameter solving module; and wherein the one or more processors are further configured to communicate with or control the haptic generation module, the visual-auditory generation module, the multi-physiological signal acquisition module, and the multi-sensory signal acquisition module; and wherein as a core of the affective haptic regulation system based on multimodal fusion, the haptic optimal parameter adjustment module automatically seeks for a haptic parameter with the help of an optimization theory according to the difference between the current affective state and the target emotion of the user, and sends the haptic parameter to the haptic generation module to ensure the effectiveness of affective regulation; and the haptic optimal parameter adjustment module comprises a haptic parameter optimization model and a haptic parameter solving module.

2. The affective haptic regulation system based on multimodal fusion according to claim 1, wherein the haptic parameter optimization model is expressed as:

$$\min_{f,q,r,c} \gamma \sum_{i=1}^{n} \|M_i(f, q, r, c) - M_{bi}\|_2^2 + \mu\|S(f, q, r, c) - S_b\|_2^2 + \varphi\|P(f, q, r, c)\|_2^2$$

$$\text{s.t. } 0 \le P \le P_m$$

$$0 \le f \le f_m$$

$$0 \le q \le q_m$$

$$0 \le r \le r_m$$

wherein $M_i$ is an actual power value of a certain electrode i on a brain topographic map, $M_{bi}$ is a reference power value of the certain electrode i on the brain topographic map, S is a calculated affective state value, Sis a target affective state value, P is an actual power value consumed by the haptic generation module, $P_m$ is a set maximum power value consumed by the haptic generation module, $f_m$ is a set maximum haptic vibration frequency, $q_m$ is a set maximum haptic vibration intensity, $r_m$ is a set maximum haptic vibration rhythm, and $\gamma$, $\mu$ and $\varphi$ are weight coefficients of the haptic parameter optimization model.

3. The affective haptic regulation system based on multimodal fusion according to claim 1, wherein the haptic parameter solving module adopts a machine learning algorithm to solve four parameters in the haptic parameter optimization model, that is, a haptic vibration frequency f, a haptic vibration intensity q, a haptic vibration rhythm r, and a haptic vibration position c, and to send the solved parameters to the haptic generation module.

4. The affective haptic regulation system based on multimodal fusion according to claim 1, wherein the haptic generation module is a wearable device capable of expressing haptic sensation through vibration, comprising a vibration vest, a vibration bracelet, and vibration gloves, and the haptic generation module is configured to transmit specific haptic experience by setting a vibration frequency, a vibration intensity, a vibration rhythm and a vibration position of a haptic generation device; and the haptic generation module exhibits continuous presence of a background haptic vibration that changes adaptively with audio, and another haptic expression can be realized based on the four parameters calculated by the haptic parameter optimization model, and the haptic expression corporates with the background haptic vibration to enhance affective experience of the user.

5. The affective haptic regulation system based on multimodal fusion according to claim 1, wherein the visual-auditory generation module provides the user with visual and auditory stimuli, comprising movie clips of different emotion types; and the movie clips are conducive to guiding the user to enter a specific affective state, and audio of the movie clips provides a basis for changes in the background haptic vibration.

6. The affective haptic regulation system based on multimodal fusion according to claim 1, wherein the multi-physiological signal acquisition module acquires a plurality of physiological signals of the user in real time, comprising 64-channel electroencephalogram (EEG) signals and electrocardiogram (ECG) signals; the EEG signals are acquired by an EEG signal acquisition module, and the EEG signal acquisition module is composed of a 64-channel actiCAP electrode cap and an EEG amplifier from Brain Products GmbH; and the ECG signals are acquired by an ECG signal acquisition module, and the ECG signal acquisition module is an ActiveTwo series high-channel ECG acquisition system from Biosemi B.V.

7. The affective haptic regulation system based on multimodal fusion according to claim 1, wherein the multi-sensory signal acquisition module comprises an auditory signal acquisition module and a haptic signal acquisition module, which are capable of acquiring audio signals generated in the visual-auditory generation module in real time, and acquiring the haptic vibration signals generated in the haptic generation module in real time, respectively.

8. The affective haptic regulation system based on multimodal fusion according to claim 1, wherein the multimodal fusion emotion recognition module is capable of analyzing, processing and recognizing the current affective state of the user according to multi-physiological signals of the user and multi-sensory signals of emotion elicitation materials, and then sending a signal of the current affective state to the haptic optimal parameter adjustment module for intelligent regulation of a haptic parameter; the multimodal fusion emotion recognition module comprises a signal preprocessing module, a feature extraction module, a feature fusion module, and an emotion decoding module; the signal preprocessing module pre-processes the acquired EEG signals and the ECG signals, comprising downsampling, filtering, artifact removal, and the like; the feature extraction module extracts features from the audio signals, the haptic vibration signals, the preprocessed EEG signals and ECG signals, respectively; the feature fusion module performs feature fusion on multi-physiological signal features, audio features extracted from the audio signals and vibration features extracted from the haptic vibration signals by using a feature fusion algorithm; the emotion decoding module classifies the multimodal fusion features by using a classification algorithm to obtain the current affective state of the user; and the multimodal fusion emotion recognition module has the advantage of fusing the multi-physiological signal features with audio and haptic modal features, effectively reducing the influence of unstable physiological signals on emotion recognition results.

9. A regulation method generated by the affective haptic regulation method based on multimodal fusion according to claim 1, comprising the following implementation steps:

step S1: applying visual-auditory-haptic fusion stimuli; wherein the user is guided into different affective states by presenting visual-auditory stimuli and haptic stimuli;

wherein the visual-auditory stimuli are composed of 16 movie clips of about 4 minutes, covering four types of emotion: happiness, sadness, fear and calmness, and each of the types of emotion corresponds to 4 movie clips;

wherein the haptic stimuli comprise continuous presence of the background haptic vibration that changes adaptively with audio, and a haptic effect with vibration parameters determined by the haptic optimal parameter adjustment module; and wherein after each of the movie clips ends, the user conducts a self-assessment of 20 s, that is, actual feeling of the movie clips, which is used to verify the effectiveness of the experiment; and afterwards, the user will rest for 30 s to prepare for a next round of playing of the move clips;

step S2: performing multimodal acquisition, comprising multi-physiological signals and multi-sensory signals;

wherein EEG signals, ECG signals, the audio signals, and haptic vibration signals of the user are acquired in real time; the EEG signals are acquired by the EEG signal acquisition module composed of the 64-channel actiCAP electrode cap and the EEG amplifier from Brain Products GmbH; the ECG signals are acquired by the ECG signal acquisition module composed of the ActiveTwo series high-channel ECG acquisition system from Biosemi B.V.; and the audio signals are acquired by the auditory signal acquisition module, and the haptic vibration signals are acquired by the haptic signal acquisition module;

step S3: performing multimodal feature extraction and feature fusion;

wherein the acquired EEG signals and the ECG signals are preprocessed, comprising downsampling, filtering, artifact removal, and the like, to ensure the quality and stability of the signals; features are then extracted from the preprocessed EEG and ECG signals to obtain EEG and ECG signal features of the user, and these features can capture variation patterns of different physiological signals in different affective states; furthermore, the audio features are extracted from the audio signals, and the haptic vibration features are extracted from the haptic vibration signals; and the feature fusion algorithm is adopted to fuse the multi-physiological signal features with the audio features and the haptic vibration features to enhance the accuracy and robustness of emotion recognition;

step S4: decoding multimodal fusion emotion and giving feedback;

wherein the multimodal fusion features are classified by using the classification algorithm to obtain the current affective state of the user, and the current affective state is then sent back to the haptic optimal parameter adjustment module;

step S5: solving and updating the vibration parameters;

wherein the haptic optimal parameter adjustment module receives the current affective state of the user, automatically solves the optimal haptic parameter according to the difference between the current emotion and the target emotion, and sends the optimal haptic parameter to the haptic generation module and generates the haptic effect, so as to ensure that the applied haptic stimuli match an actual affective need of the user, and step S6: finishing the experiment and establishing an affective haptic database;

wherein completion of the playing of the 16 movie clips indicates that the entire experiment is finished, and the vibration parameters corresponding to different affective states of the user are the analyzed, and the affective haptic database of the user is then established; and different vibration parameters are mapped to different affective states, and a personalized haptic mode is generated to present diverse affective experience for the user.

* * * * *